United States Patent
Takács et al.

(10) Patent No.: US 6,574,913 B2
(45) Date of Patent: Jun. 10, 2003

(54) SEMIOCHEMICAL AND SONIC SIGNALS FOR MONITORING AND CONTROL OF CLOTHES MOTHS

(76) Inventors: Stephen J. Takács, 108 South Springer, Burnaby, British Columbia (CA), V5B 3K3; Gerhard J. Gries, 484 Cariboo Crescent, Coquitlam, British Columbia (CA), V3C 4X7; Regine M. Gries, 484 Cariboo Crescent, Coquitlam, British Columbia (CA), V3C 4X7

( * ) Notice: Subject to any disclaimer, the term of this patent is extended or adjusted under 35 U.S.C. 154(b) by 0 days.

(21) Appl. No.: 09/912,344

(22) Filed: Jul. 26, 2001

(65) Prior Publication Data

US 2003/0019440 A1 Jan. 30, 2003

(51) Int. Cl.[7] .......................... A01M 1/02; A01N 25/00
(52) U.S. Cl. ............................. 43/107; 424/84; 119/719
(58) Field of Search ..................... 119/6.5, 719; 43/107

(56) References Cited

U.S. PATENT DOCUMENTS

| | | | | |
|---|---|---|---|---|
| 4,404,185 A | * | 9/1983 | Maccone et al. | 424/84 |
| 4,610,876 A | * | 9/1986 | Underhill et al. | 424/84 |
| 4,693,890 A | * | 9/1987 | Wilson et al. | 424/78 |
| 4,696,676 A | * | 9/1987 | Wilson et al. | 44/7.5 |
| 4,845,131 A | | 7/1989 | Behrenz et al. | |
| 5,170,583 A | * | 12/1992 | Coaker et al. | 43/107 |
| 5,311,697 A | | 5/1994 | Cavanaugh et al. | 43/132.1 |
| 5,665,344 A | * | 9/1997 | Pair et al. | 424/84 |
| 5,750,129 A | * | 5/1998 | Wakarchuk | 424/408 |
| 5,772,983 A | * | 6/1998 | O'Connell et al. | 424/9.2 |
| 6,074,634 A | * | 6/2000 | Lopez, Jr. et al. | 424/84 |
| 6,190,652 B1 | * | 2/2001 | Pair et al. | 424/84 |
| 6,190,653 B1 | * | 2/2001 | Landolt et al. | 424/84 |
| 6,264,939 B1 | * | 7/2001 | Light et al. | 424/84 |
| 2002/0011020 A1 | * | 1/2002 | Nelson et al. | 43/107 |

OTHER PUBLICATIONS

Database BIOSIS 'Online! Biosciences Information service, Philadelphia, PA, US; 1989; Szocs G. et al.: "2 13 and 3 13 Octadecadienyl Compounds Composing Sex Attractants for Tineid and Sesiid Moths Lepidoptera"; Database accession No. PREV199089026470 XP002221073; abstract; & *Biochemical Systematics and Ecology*, vol. 17, No. 5, 1989, p. 417–422, ISSN: 0305–1978.

Database BIOSIS 'Online! Biosciences Information Service, Philadeophia, PA, US; 1996; Trematerra P. et al.: "Monitoring of webbing clothes moth, *Tineola bisselliella* (Hummel), by sex pheromone"; Database accession No. PREV199699182673 XP 002221074; abstract; & *Anzeiber Fuer Schaedlingskunde Pflanzenschutz Umweltschutz*, vol. 69, No. 5, 1996, p. 119–121; ISSN: 0340–7330.

Database CAB 'Online! CAB International, Wallingford, Oxon, GB; S. Takacs et al.: "Semiochemical–mediated location of host habitat by *Apantales carpatus* (Say) (Hymenoptera: Braconidae), a parasitoid of clothes moth larvae" retreived from STN–International; Database accession No. 97:129534 CABA XP002221075; abstract; & *Journal of Chemical Ecology*, vol. 3, No. 2, 1997, p. 459–472.

S. Takacs et al.,: "Communication ecology of webbing clothes moth: 4. Identification of male–and female–produced pheromones", *Chemecology*, vol. 11, No. 4, 2001, p. 153–159, XP002221071.

S. Takacs et al.,: "Where to find a mate? Resource–based sexual communication of webbing clothes moth", *Naturwissenschaften*, vol. 89, 2002, p. 57–59, SP002221072, Berlin, DE.

Database BIOSIS 'Online! Biosciences Information Service, Philadelphia, PA, US; August 2001, Takacs Stephen et al.: "Communication ecology of webbing clothes moth: 2. Identification of semiochemicals mediating attraction of adults to larval habitat"; Database accession No. PREV200100442312 XP002221076; abstract, & *Journal of Chemical Ecology*, vol. 27, No. 8, Aug. 2001, p. 1547–1560; ISSN: 0098–0331.

Database CA 'Online! Chemical Abstracts Service, Columbus, Ohio, US; R. Yamaoka et al.: "Structure elucidation of Koiganal I and II, the sex perhomones of the webbing clothes moth, using capillary GC/MS" retrieved from STN–International; Database accession No. 104:17841 CA XP002221077; abstract; & *Shitsuryo Bunseki*, vol. 33, no. 3, 1985, p. 189–195.

Database CROPU 'Online! D.K. Mueller: "The pratical use of the new pheromone for webbing clothes moth (*Tineola bisselliella*)" retrieved from STN–International; Database accession No. 1996–83104 CROPU XP002221078; abstract; & *Procbrit. Pest Contr. Assoc. Conf.*, 1995, p. 123–124.

(List continued on next page.)

Primary Examiner—Charles T. Jordan
Assistant Examiner—Bret Hayes
(74) Attorney, Agent, or Firm—Oyen Wiggs Green & Mutala

(57) ABSTRACT

This invention relates to a composition and procedure for manipulating the behaviour of the webbing clothes moth, *Tineola bisselliella* (Hummel) (Lepidoptera: Tineidae). In particular, this invention relates to the use of specific semiochemical and sonic signals for manipulating the behaviour of the webbing clothes moths. A composition of chemicals for manipulating the behaviour of clothes moths, said composition comprising two or more chemicals in all possible combinations and ratios selected from the group consisting of: 1) (E,Z)-2,13:octadecadienal; 2) (E,Z)-2, 13:octadecadienol; 3) hexadecanoic acid methyl ester; 4) (Z)-9-hexadecenoic acid methyl ester; 5) nonanal; 6) geranylacetone; 7) octanal; 8) decanal; 9) nonenal; 10) octenal; 11) decenal.

18 Claims, 17 Drawing Sheets

OTHER PUBLICATIONS

Database WPI, Section PQ, Week 199931; Derwent Publications Ltd., London, GB; Class P14, AN 1999–371461 XP002221079 & ZA 9 806 812 A (Grinaker Electronics Ltd.), Apr. 28, 1999; abstract.

P.D. Cox, et al., Monitoring populations of the webbing clothes moth, *Tineola Bisselliella*, using pheromone lures. In: K.B. Wildey (ed.) Proceedings of the second International Conference on Insect Pests in the Urban Environment, 541–545.

P. Trematerra and F. Fontana, Monitoring of webbing clothes moth. *Tineola bisselliella* (Hummel), by sex pheromone, *Anz. Schadlingskunde Pflanzenschutz Umweltschutz* 69, 119–121 (1996).

* cited by examiner

Sonic signal from ♂ WCM

Sonic signal from ♂ WCM when conspecifics are nearby

US 6,574,913 B2

SEMIOCHEMICAL AND SONIC SIGNALS FOR MONITORING AND CONTROL OF CLOTHES MOTHS

FIELD OF THE INVENTION

This invention relates to a composition and procedure for manipulating the behaviour of the webbing clothes moth, *Tineola bisselliella* (Hummel) (Lepidoptera: Tineidae). In particular, this invention relates to the use of specific semiochemical and sonic signals for manipulating the behaviour of the webbing clothes moths.

BACKGROUND OF THE INVENTION

Webbing clothes moths, *Tineola bisselliella* (Hum.) (Lepidoptera: Tineidae), invade and cause damage in households, textile and fur warehouses, and museums throughout the world (1–3). In temperate regions, they are economically important, causing hundreds of millions of dollars of damage in North America each year (4).

*T. bisselliella* inhabits well-sheltered bird nests, dry corpses and animal lairs that are not exposed to direct light (5–7). Adults have vestigial mouthparts and do not cause damage. Larvae, however, feed year round on keratin contained in woollen goods, hair, feathers, and other animal-based products like clothing, rugs, and furniture (5). Exploratory feeding also damages synthetic textiles (8).

Pesticides are used to treat or prevent larval infestations of *T. bisselliella*. Physical control methods include vacuum (3), repeated cooling and heating (9), and sanitation of potential infestation sites (2, 4). Use of naturally occurring chemicals for control of *T. bisselliella* is increasingly preferred by the public (4). These chemicals include feeding inhibitors, repellents, and plant-based insecticides (10, 11). There is no suitable method yet for detection of incipient infestations.

Semiochemicals (message-bearing chemicals) that attract *T. bisselliella* to larval habitat and intra-specific sexual communication signals have hardly been investigated. Larva and adult *T. bisselliella* are attracted to fishmeal, fish oil, and dried meat (12). Females select oviposition sites based on their physical stimuli (13), or volatiles (14). E2, Z13-Octadecadienal and E2-octadecenal are reported sex pheromone components of *T. bisselliella* (15), but these compounds are only moderately attractive (16, 17) and unreliable for practical control situations (T. Konicek, person. communication).

There are many patents listed in the patent database under the keyword *T. bisselliella* (scientific species name for webbing clothes moth) or misspellings thereof. Most of these patents are concerned with pesticides, reporting that insects including clothes moths are killed by active ingredient(s). These active ingredients are very different from the attractive semiochemicals claimed in the subject application. Other patents are concerned with pest control devices, such as U.S. Pat. No. 4,484,315 "Ultrasonic Pest Control Device" (20), or U.S. Pat. No. 4,616,351, "Pest Control Apparatus" (19), reporting the use of ultrasonic waves for control of pests, including clothes moths. The frequency of sonic waveforms as claimed for attraction and control of *T. bisselliella* in the subject application is in the audible low frequency range. Additional patents are concerned with chemicals that repel keratin-feeding pests including clothes moths. Diphenylurea and one synthetic pyrethroid (U.S. Pat. No. 5,057,539) (20), isoborneol (U.S. Pat. No. 4,845,131) (21), pyridyloxytrifluoromethanesulfonanilides (U.S. Pat. No. 4,731,090) (22), 5-pyridyloxy- or thiothenylcarbamoyl)barbituric acid (U.S. Pat. No. 4,602,912) (23), 5-phenylcarbamoylbarbituric acid (U.S. Pat. No. 4,283,444) (24), N'-alkyl-N'-(3,5-dimethylbenzoyl)-N-(substituted benzoyl)-hydrazine (U.S. Pat. No. 5,358,967) (25), phenoxytrifluoromethanesulfoanilides (U.S. Pat. No. 4,664,673) (26), and incense cedar associated with a multi-garment hanger device (U.S. Pat. No. 5,582,334) (27) are all claimed to protect keratinous material from attack by insects that feed on keratin. All these repellents are very different from the attractive semiochemicals claimed in this application.

SUMMARY OF THE INVENTION

We reveal stimuli which singly or in combination attract male and female *T. bisselliella*. These stimuli include: 1. semiochemicals from larval habitat (mainly nonanal and geranylacetone) that attract males and females; 2. female-produced sex pheromone components [(E, Z)-2,13:octadecadienol and (E,Z)-2,13:octadecadienal] that attract males; 3. male-produced sex pheromone components (hexadecanoic acid methyl ester and Z9-hexadecenoic acid methyl ester) that attract males and females; and 4. male-produced sonic signals (primary frequencies: 50+/−10 Hz; 70/+−10 Hz; 110+/−20 Hz; 140+/−20 Hz and their harmonics) that attract males and females. We further reveal that combinations of these signals result in a bait optimally attractive to male and female *T. bisselliella*.

The essence of the invention is the preparation and implementation of these stimuli for manipulating the behaviour of *T. bisselliella*. Stimuli can be used in all possible combinations and ratios. Stimuli compositions can be contained in, and emitted from, slow release devices or sonic microchips. Devices can be held in traps to capture attracted male and female *T. bisselliella*. The invention can be used as a diagnostic tool to help decide whether and when control of insects that feed on fur, fabric and other keratin containing products is warranted and as a means for protection of fur, fabric and other keratin containing products.

The invention is directed to a composition of chemicals for manipulating the behaviour of clothes moths, said composition comprising two or more chemicals in all possible combinations and ratios selected from the group consisting of: 1) (E,Z)-2,13:octadecadienal; 2) (E,Z)-2,13:octadecadienol; 3) hexadecanoic acid methyl ester; 4) (Z)-9-hexadecenoic acid methyl ester; 5) nonanal; 6) geranylacetone; 7) octanal; 8) decanal; 9) nonenal; 10) octenal; 11) decenal.

The invention is also directed to a sonic signal for manipulating the behaviour of clothes moths, said signal comprising one or more frequencies in all possible combinations and ratios selected from the group consisting of: 1) 50+/−10 Hz; 2) 110+/−20 Hz; 3) 70+/−10 Hz; 4) 140+/−10 Hz; 5) 165+/−30; 6) 220+/−40; 7); 280+/−40 Hz.

The invention is also directed to a combination of chemical and sonic signals for manipulating the behaviour of clothes moths, said combination comprising a composition of two or more chemicals in all combinations and ratios selected from the group consisting of: 1) (E,Z)-2,13:octadecadienal; 2) (E,Z)-2,13:octadecadienol; 3) hexadecanoic acid methyl ester; 4) (Z)-9-hexadecenoic acid methyl ester; 5) nonanal; 6) geranylacetone; 7) octanal; 8) decanal; 9) nonenal; 10) octenal; 11) decenal, and a sonic signal of one or more frequencies in all combinations and ratios selected from the group consisting of: 1) 50+/−10 Hz; 2) 110+/−20 Hz; 3) 70+/−10 Hz; 4) 140+/−10 Hz; 5) 165+/−30; 6) 220+/−40; 7); 280+/−40 Hz.

The composition can be contained in, or released from, slow release devices. The composition can be contained in, and released from, a trap that captures attracted T. bisselliella.

The signal can be generated by a sonic apparatus contained in or associated with a trap that captures attracted T. bisselliella. The sonic apparatus can be an electronically activated sonic microchip.

The invention is also directed to an apparatus for attracting clothes moths, said apparatus containing a composition comprising two or more chemicals in all possible combinations and ratios selected from the group consisting of: 1) (E,Z)-2,13:octadecadienal; 2) (E,Z)-2,13:octadecadienol; 3) hexadecanoic acid methyl ester; 4) (Z)-9-hexadecenoic acid methyl ester; 5) nonanal; 6) geranylacetone; 7) octanal; 8) decanal; 9) nonenal; 10) octenal; 11) decenal.

The apparatus of the invention can emit a sonic signal for manipulating the behaviour of clothes moths, comprising one or more frequencies in all possible combinations and ratios selected from the group consisting of: 1) 50+/−10 Hz; 2) 110+/−20 Hz; 3) 70+/−10 Hz; 4) 140+/−10 Hz; 5) 165+/−30; 6) 220+/−40; 7); 280+/−40 Hz.

The apparatus for attracting clothes moths can contain a combination of chemical and sonic signals for manipulating the behaviour of clothes moths, said combination comprising a composition of two or more chemicals in all combinations and ratios selected from the group consisting of: 1) (E,Z)-2,13:octadecadienal; 2) (E,Z)-2,13:octadecadienol; 3) hexadecanoic acid methyl ester; 4) (Z)-9-hexadecenoic acid methyl ester; 5) nonanal; 6) geranylacetone; 7) octanal; 8) decanal; 9) nonenal; 10) octenal; 11) decenal, and a sonic signal of one or more frequencies in all combinations and ratios selected from the group consisting of: 1) 50+/−10 Hz; 2) 110+/−20 Hz; 3) 70+/−10 Hz; 4) 140+/−10 Hz; 5) 165+/−30; 6) 220+/−40; 7); 280+/−40 Hz. The apparatus can contain an insect capturing adhesive.

The invention is also directed to a bait and trap for deployment in an area containing fur, fabric or other keratin containing products comprising a fur, fabric or other keratin feeding insect bait, said bait incorporating a composition of chemicals, or sonic signals, or a combination of a composition of chemicals and sonic signals according to the invention, and a trap which can have openings which can enable the insects to enter the trap and a barrier or retainer which can prevent the insects from leaving the trap.

The invention also pertains to a method of manipulating the behaviour of insects that feed on fur, fabric and other keratin containing products which comprises exposing the insects to one or more chemicals or sonic signals according to the invention.

The invention also pertains to a method of diagnosing whether protection of fur, fabric or other keratin containing products is warranted, comprising exposing the fur, fabric or other keratin containing product to a composition of one or more semiochemicals or sonic signals according to the invention and determining whether any fur, fabric or keratin containing products consuming insects are attracted by the composition of semiochemicals or the sonic signals.

The invention includes a method of protecting fur, fabric or other keratin containing product from attack by fur, fabric or other keratin containing product consuming insects by deploying proximate to the fur, fabric or other keratin containing product a composition of semiochemicals or sonic signals according to the invention.

DRAWINGS

Drawings illustrate specific embodiments of the invention, but should not be construed as restricting the spirit or scope of the invention in any way:

DETAILED DESCRIPTION OF INVENTION

Figure 1:
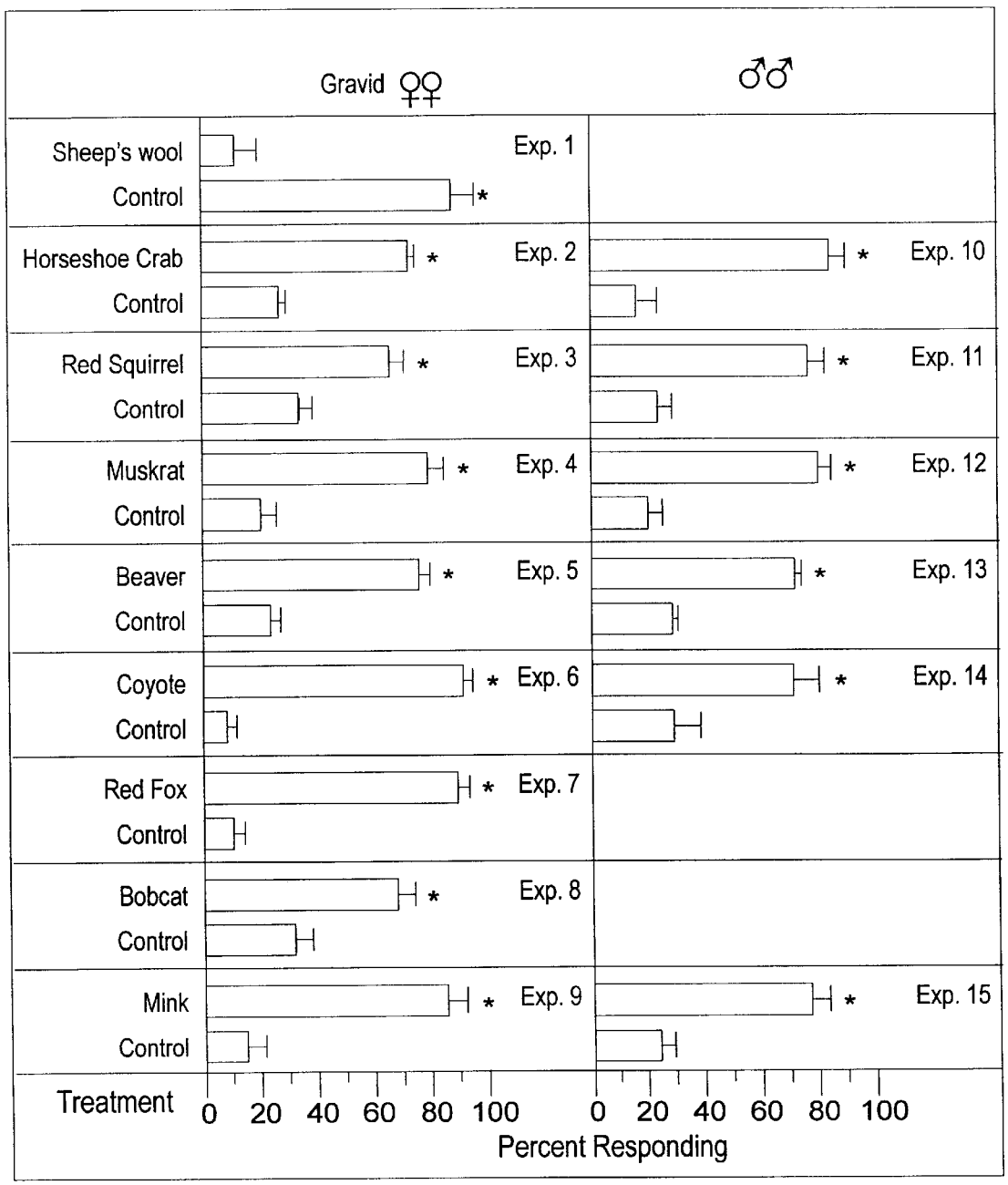
FIG. 1 illustrates graphical data of captures of female or male T. bisselliella in traps baited with potential larval habitat.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

1. Attraction of Male and Female *T. bisselliella* to Larval Habitat

Natural larval habitat tested in choice experiments included sheep's wool (freshly sheared or aged 1 year), specimens of horseshoe crab (dry formaldehyde-preserved) and samples (100 cm$^2$) of untanned, dried animal pelts.

Tactic responses of *T. bisselliella* to volatile stimuli from larval habitat were assessed in a closed cylindrical Plexiglas container (125 cm diameter, 60 cm height). Thin cardboard discs (10 cm diameter) coated with Tanglefoot on the upper side were placed on the arena floor 80 cm apart from each other. Platforms suspended above the centre of the coated discs supported randomly assigned test or control stimuli. Control stimuli consisted of cardboard silhouettes visually resembling test stimuli. Per experiment 10 replicates with 25 adult moths each were employed. Moths were released during the scotophase from a Petri dish in the centre of the arena after 30-min of acclimation. After 12 hours of experimental time, moths captured on sticky discs (FIG. 1) were recorded as responders and statistically analysed.

FIG. 1 illustrates graphical data of captures of female or male *T. bisselliella* in traps baited with larval habitat. Asterisks on bar indicate a significant difference [Wilcoxon paired-sample test (P<0.05)].

2. Capture, Analysis and Bioassays of Habitat-Derived Volatiles

Samples of animal pelt (150 cm$^2$) were aerated for one week in a cylindrical Pyrex glass chamber. A water-aspirator was used to draw charcoal-filtered, humidified air at 2 L/min through the chamber and a glass column (14 cm×13 mm O.D.) filled with Porapak Q. Volatiles captured on Porapak Q were eluted with 5 ml of redistilled pentane and the eluent concentrated to 2 ml by distillation in a 30 cm Dufton column, adjusting the volatile extract so that 2 $\mu$l equalled 5 pelt-min of volatile collection. Aliquots of 2.5 pelt-min equivalents of Porapak Q-captured volatile extracts were analysed by coupled gas chromatographic-electroantennographic detection (GC-EAD) (28) (FIG. 2).

Figure 2:
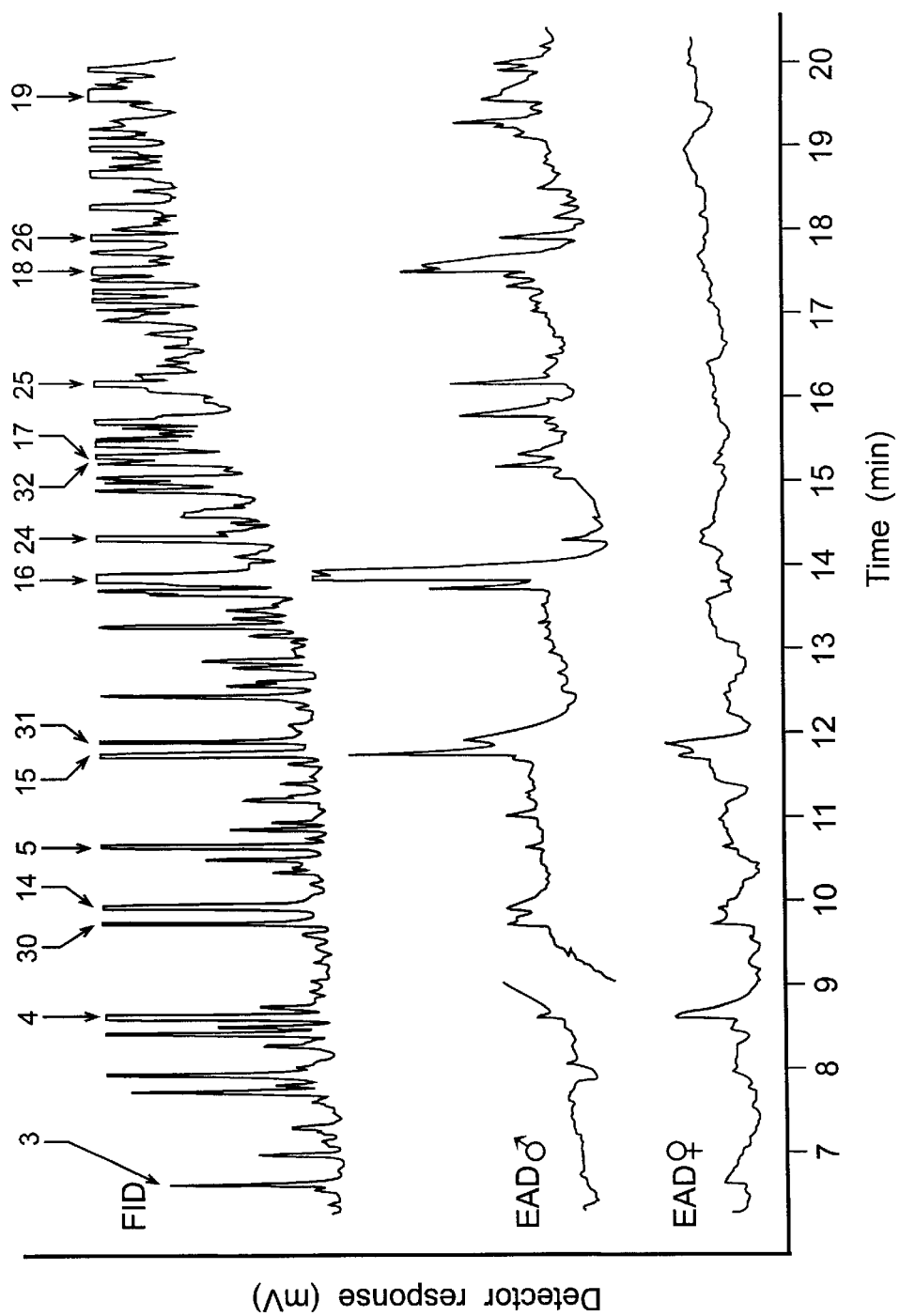
FIG. 2 illustrates flame ionization detector (FID) and electroantennographic detector (EAD ♂: male T. bisselliella antenna; EAD ♀: gravid female T. bisselliella antenna) responses to 5 pelt-min of squirrel pelt volatile extract.

FIG. 2 illustrates flame ionization detector (FID) and electroantennographic detector (EAD ♂: male *T. bisselliella* antenna; EAD ♀: gravid female *T. bisselliella* antenna) responses to 5 pelt-min of squirrel pelt volatile extract. Chromatography: Hewlett Packard (HP) 5890A gas chromatograph equipped with a fused silica column (30 m×0.25 mm ID) coated with DB-5; linear flow velocity of carrier gas: 35 cm/sec; injector and FID detector temperature: 240° C.; temperature program: 1 min at 50° C., 20° C./min to 70° C. then 7.5° C./min to 280° C. (J & W Scientific, Folsom, Calif. 95630). EAD-active compounds were analyzed by GC-mass spectrometry (MS) in full scan electron impact (EI) and chemical ionization (isobutane) (CI) modes, using a Varian Saturn II Ion Trap GC-MS and a HP 5985B GC-MS. Antennally-active compounds were identified as follows: 1. hexanal (20.0); 2. heptanal (35.0); 3. octanal (55.0); 4. nonanal (80.0); 5. decanal (20.0); 6. dodecanal (4.0); 7. tridecanal (6.0); 8. tetradecanal (5.0); 9. pentadecanal (0.8); 10. hexadecanal (1.0); 11. heptadecanal (0.7); 12. octadecanal (0.1); 13. heptanol (10.0); 14. nonanol (10.0); 15. decanol (12.0); 16. undecanol (200.0); 17. dodecanol (10.0); 18. tridecanol (70.0); 19. tetradecanol (3.0); 20. pentadecanol (2.0); 21. hexadecanol (0.3); 22. heptadecanol (0.5); 23. octadecanol (0.1); 24. tetradecane (20.0); 25. pentadecane (100.0); 26. hexadecane (100.0); 27. eicosane (20.0); 28. uneicosane (0.7); 29.2-undecanal (4.0); 30. E2-nonenal (9.0); 31. E2-decenal (11.0); 32. geranylacetone (1.0). Numbers in brackets refer to nanogram quantities present in 15 pelt-min of aeration of dried, untanned animal pelt (150 cm$^2$).

Figure 3:
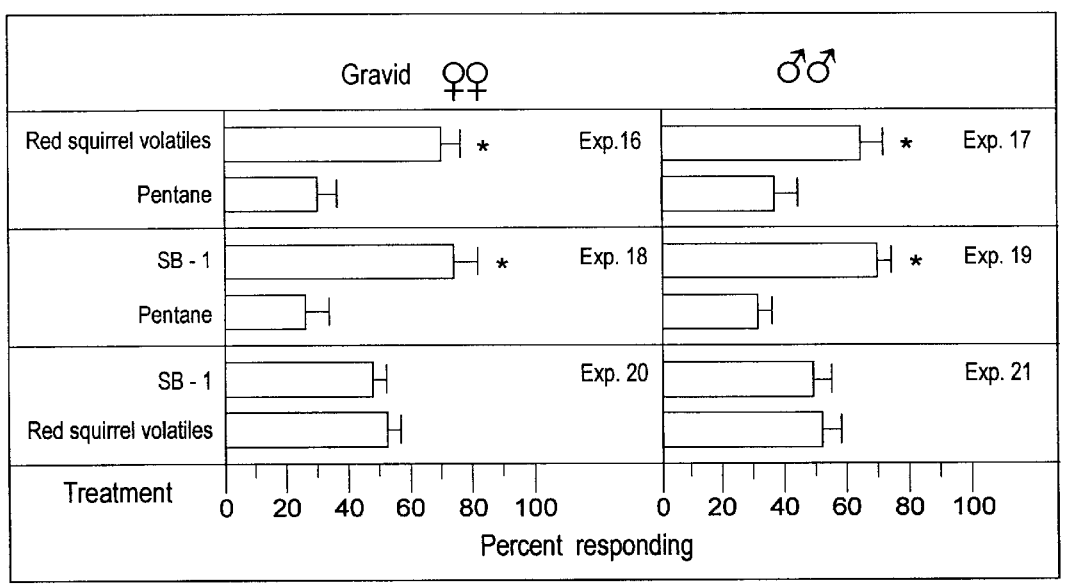
FIG. 3 illustrates graphical data of captures of female or male T. bisselliella in traps baited with natural or synthetic volatiles from larval habitat.

In arena bioassay experiments (following the general protocol as described on page 7, lines 22–31, paragraph [0041]) male and gravid female *T. bisselliella* preferred Porapak Q volatile extract from red squirrel pelt over a pentane control (Exp. 16, 17), and also a blend of 29 synthetic squirrel pelt volatiles (SB-1) over a pentane control (Exps. 18, 19) (FIG. 3).

FIG. 3 illustrates graphical data of captures of female or male *T. bisselliella* in traps baited with Porapak Q volatile extract from red squirrel pelt (75 pelt-min), a blend of synthetic pelt volatiles (SB-1) or a pentane solvent control. Compounds in SB-1 consisted of nonanal (400.0); decanal (100.0); 6. dodecanal (20.0); 7. tridecanal (24.0); 8. tetradecanal (25.0); 9. pentadecanal (4.0); 10. hexadecanal (5.0); 11. heptadecanal (3.5); 12. octadecanal (0.5); 13. heptanol (50.0); 14. nonanol (50.0); 15. decanol (60.0); 16. undecanol (1000.0); 17. dodecanol (100.0); 18. tridecanol (350.0); 19. tetradecanol (15.0); 20. pentadecanol (10.0); 21. hexadecanol (1.5); 22. heptadecanol (1.5); 23. octadecanol (0.5); 24. tetradecane (100.0); 25. pentadecane (500.0); 26. hexadecane (500.0); 27. eicosane (100.0); 28. uneicosane (3.5); 29. 2-undecanal (20.0); 30. E2-nonenal (45.0); 31. E2-decenal (55.0); 32. geranylacetone (5.0).

Numbers in brackets refer to nanogram quantities. For each experimental replicate, test stimuli in traps were dispensed from Whatman #1 filter paper. Asterisks on bar indicate a significant difference [Wilcoxon paired-sample test (P<0.01)].

Similar attractiveness of natural red squirrel pelt volatiles and the blend of synthetic pelt volatiles (SB-1) (Exps. 20–21) indicated that all essential volatiles were present in SB-1. Two compounds in the SB-1 blend, nonanal and geranylacetone, were more attractive than natural (muskrat) pelt, when tested at equivalent quantities (FIG. 4).

Figure 4:
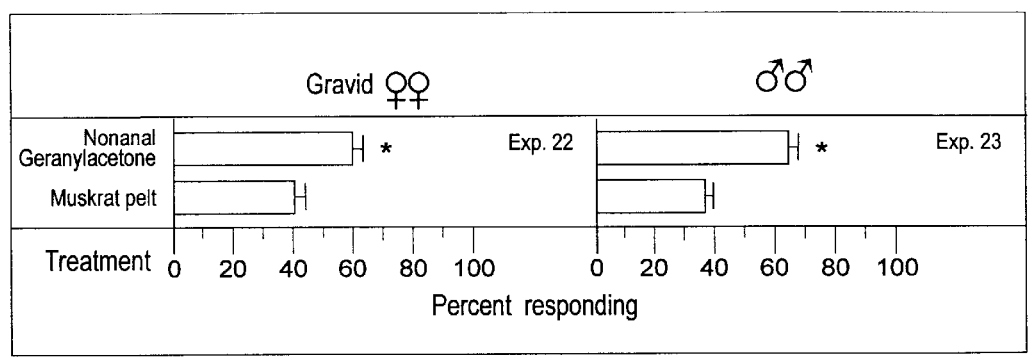
FIG. 4 illustrates graphical data of captures of female or male T. bisselliella in traps baited with the synthetic chemicals geranylacetone and nonanal or dried muskrat pelt.

FIG. 4 illustrates graphical data of captures of female or male *T. bisselliella* in traps baited with synthetic geranylacetone (44 ng) and nonanal (3.5 $\mu$g) or dried muskrat pelt [Wilcoxon paired-sample test (P<0.05)].

3. Analysis of the *T. bisselliella* Mating System

To determine the sex that emits or responds to sexual communication signals, four experiments were conducted using a bioassay with 3 interconnected identical chambers (each chamber: 10 cm diam.×2 cm height; passage 0.5 cm interior diam.×2.5 cm length) (29). For each replicate, one side chamber was randomly baited with two perforated gelatin capsules [(2.5×0.9 cm) with 7 perforations (0.3 mm) at both ends] each containing a virgin *T. bisselliella* on wool fabric while the other side chamber contained two empty perforated gelatin capsules on wool fabric. Virgin adult moths were released individually into the centre chamber 1 hour prior to dusk and their position recorded 16 hours later (1 hour after dawn). Moths in side chambers were included in statistical analyses. Each replicate employed a new device, wool fabric, and virgin moth.

Both virgin females and virgin males preferred the chamber containing capsules with male *T. bisselliella* (Exps. 24, 25). Virgin females avoided other females, and virgin males were not attracted to virgin females (Exp. 27) (FIG. 5), but exhibited excitatory behaviour in contact with capsules containing virgin females.

Figure 5:
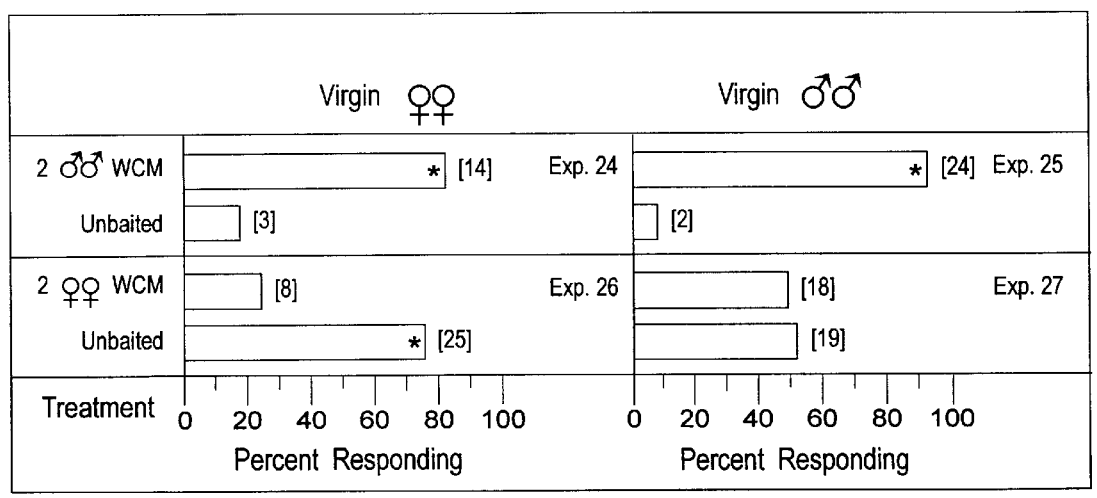
FIG. 5 illustrates graphical data of responses by adult T. bisselliella to virgin male or female T. bisselliella.

FIG. 5 illustrates graphical data of responses of adult *T. bisselliella* in binary choice bioassays to two confined virgin adult *T. bisselliella*. Numbers of individuals responding to each stimulus are given in parentheses beside bars. Asterisks indicate a significant preference for a particular treatment [Fisher Exact test (P<0.05)].

These results indicate that male *T. bisselliella* produce signals that attract males and females, and that females produce signals exciting to males only at very close range.

4. Analysis and Bioassays of Pheromone components produced by Male *T. bisselliella*

The bodies of two hundred 24–48 hour old virgin male *T. bisselliella* were extracted for 15 min in methanol. Analyses of these extracts by coupled gas chromatographic electroantennographic detection (GC-EAD) revealed 3 antennally-active compounds (FIG. 6) which were identified by GC-mass spectrometry as 1.) hexadecanoic acid methyl ester; 2.) (Z)-9-hexadecenoic acid methyl ester; and 3.) octadecanoic acid methyl ester.

Figure 6:
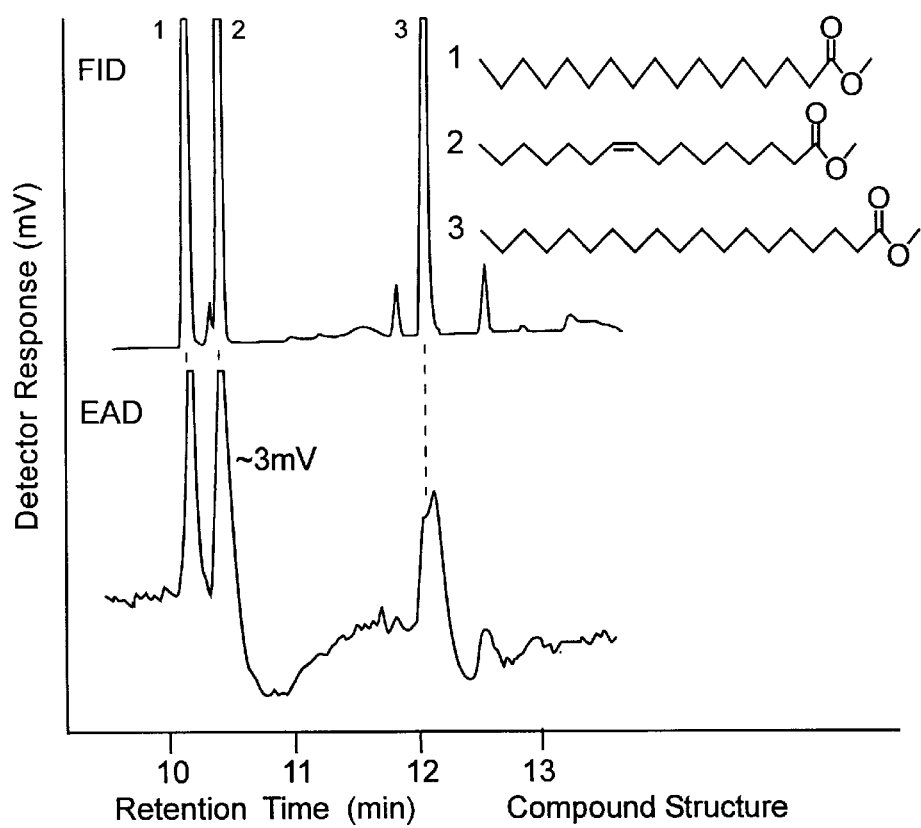
FIG. 6 illustrates flame ionization detector (FID) and electroantennographic detector (EAD: male T. bisselliella antenna) responses to one male equivalent of male T. bisselliella body.

FIG. 6 illustrates flame ionization detector (FID) and electroantennographic detection (EAD: male *T. bisselliella* antenna) responses to one male equivalent of male *T. bisselliella* body extract. EAD-active compounds 1–3 were identified by GC-mass spectrometry as 1. hexadecanoic acid methyl ester; 2. (Z)-9-hexadecenoic acid methyl ester; and 3. octadecanoic acid methyl ester. Similar responses were observed with female antennae. Chromatography: Hewlett Packard (HP) 5890A gas chromatograph equipped with a fused silica column (30 m×0.32 mm ID) coated with DB-23 (J & W Scientific, Folsom, Calif. 95630); linear flow velocity of carrier gas: 35 cm/sec; injector and FID detector temperature: 240° C.; temperature program: 1 min at 50° C., 10° C./min to 200° C. EAD-active compounds were identified by GC-mass spectrometry (MS) in full scan electron impact (EI) mode using a Varian Saturn II Ion Trap GC-MS.

Figure 7:
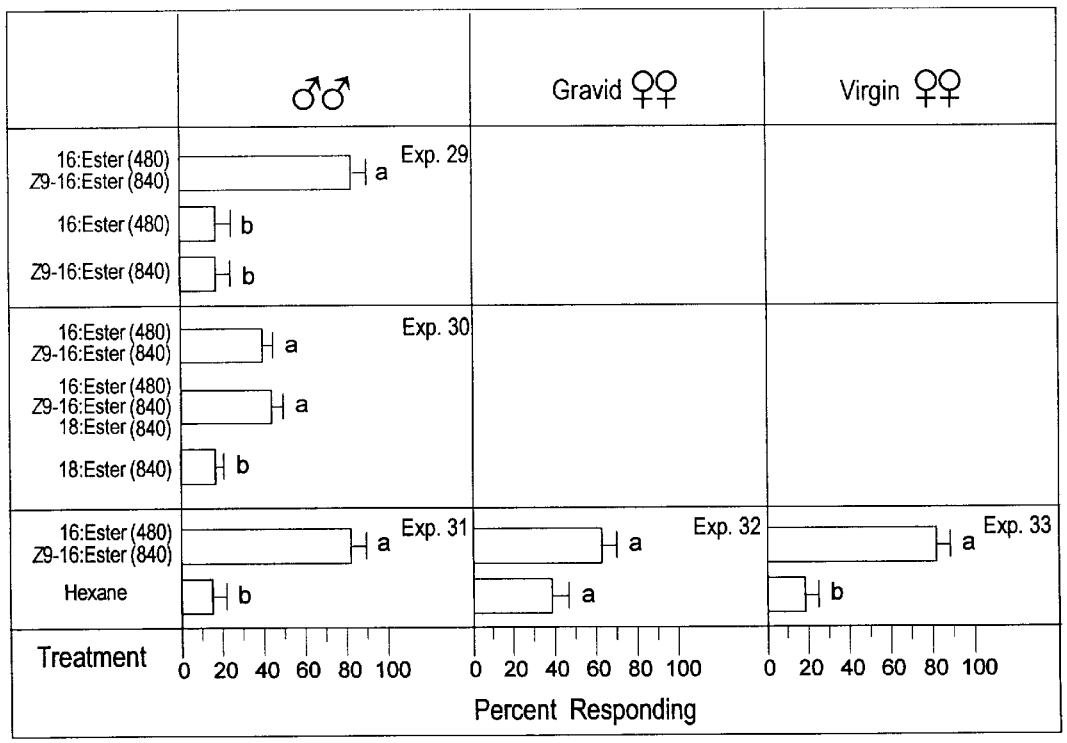
FIG. 7 illustrates graphical data of captures of male, gravid female, or virgin female T. bisselliella in traps baited with synthetic male pheromone components.

In arena bioassay experiments 29–31 (following the general protocol as described on page 7, lines 22–31, paragraph [0041]), hexadecanoic acid methyl ester and (Z)-9-hexadecenoic acid methyl ester proved to be the sex pheromone components that attracted both male and virgin female *T. bisselliella* (FIG. 7).

FIG. 7 illustrates graphical data of captures of male, gravid female, or virgin female *T. bisselliella* in traps baited with hexadecanoic acid methyl ester (16:Ester, 480 ng) plus (Z)-9-hexadecenoic acid methyl ester (Z9–16:Ester, 840 ng) or octadecenoic acid methyl ester (18:Ester, 840 ng). For each experimental replicate, test stimuli in traps were dispensed from Whatman #1 filter paper. Asterisks on bar indicate a significant difference [Wilcoxon paired-sample test (P<0.01)].

5. Analysis and Bioassays of Sonic Signals Produced by Male *T. bisselliella*

Sound produced by individual or groups of males was recorded to hard disk by a Pentium 166 computer equipped with high-speed data acquisition boards (DAQ, NI; PCI-MIO-16XE-10; 16 bit, 100 kHz maximum sampling rate). Recordings employed a ½-in condenser microphone (AKG C 460 B comb-ULS/61), phantom power supply (Atus Audio Technica CP 8508 24 V.) and signal amplification of 200 times with a differential amplifier (NI; SC-2040) and a sampling frequency of 43.2 kHz. Sonic signals recorded from male *T. bisselliella* comprised two dominant frequencies at 50+/−10 Hz and 110+/−20 Hz with 1 to 2 harmonics (165+/−30: 220+/−40) occasionally identified when other clothes moths were >5 cm from the signaller. When other moths were <5 cm from the signaller, dominant frequencies were 70+/−10 Hz and 140+/−20 Hz with 2–3 additional harmonics (210+/−30 Hz; 280+/−40 Hz) (FIG. 8).

Figure 8:
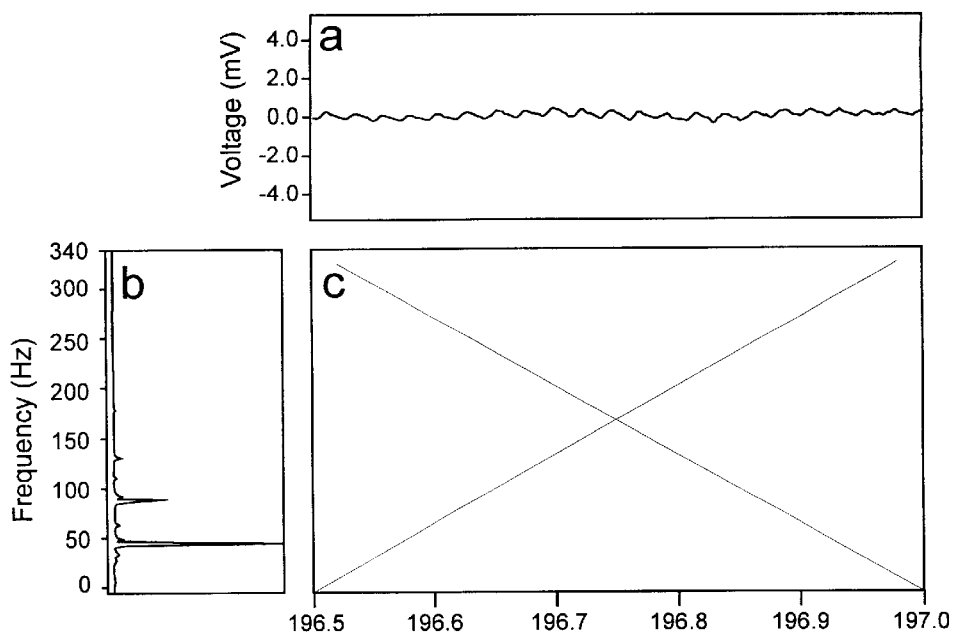
FIG. 8 illustrates waveform (a), frequency (b), and time-frequency sound intensity (c) of wing-beat caused sonic signals recorded from male T. bisselliella.
Figure 8:
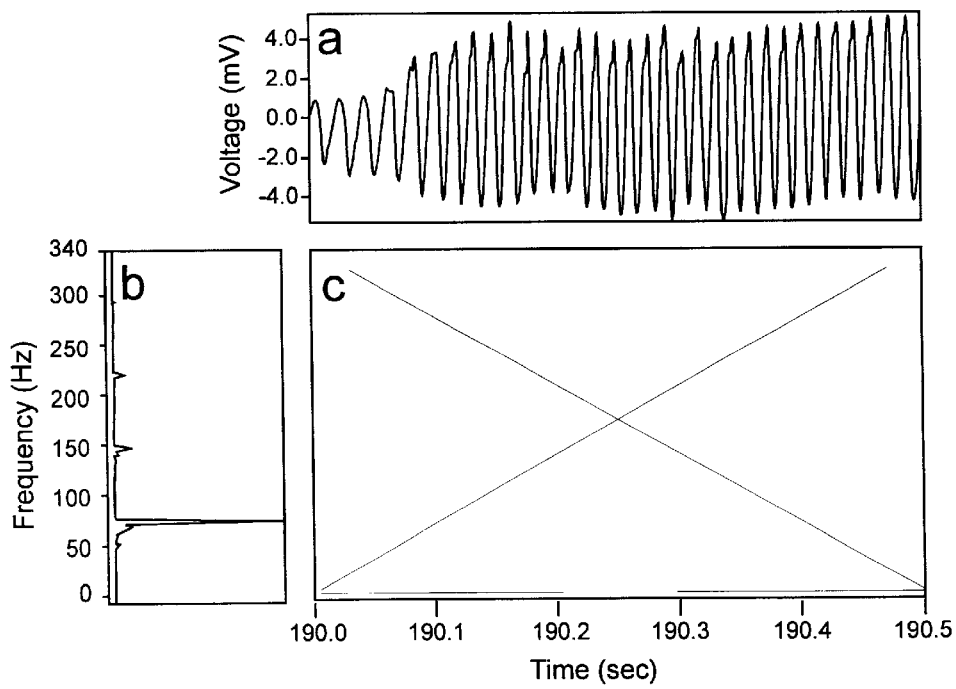

FIG. 8 illustrates waveform (a), frequency (b), and time-frequency sound intensity (c) of a sonic signal recorded from male *T. bisselliella*. Top: calling male >5 cm away from other moths; bottom: calling male <5 cm away from other. The more intense the shading in diagram c, the more intense the frequency component of the signal.

Figure 9:
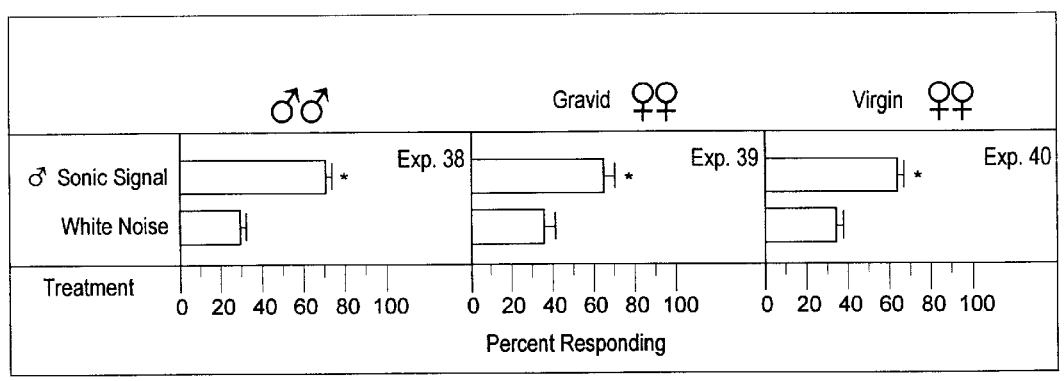
FIG. 9 illustrates graphical data of captures of male, gravid female or virgin female T. bisselliella in traps baited with sonic signals recorded from male T. bisselliella or baited with white noise.

In arena bioassay experiments (employing the general protocol as described on page 7, lines 22–31, paragraph [0041]), played-back sound from male *T. bisselliella* attracted male, gravid female and virgin female *T. bisselliella* (FIG. 9).

FIG. 9 illustrates graphical data of captures of male, gravid female or virgin female *T. bisselliella* in traps baited with sonic signals recorded from male *T. bisselliella* or baited with Gaussian white noise. Asterisks on bar indicate a significant difference [Wilcoxon paired-sample test (P<0.05)]. Recordings were digitally filtered and played back at biologically relevant levels (55 dB at 2.5 cm) through Sennheisser HV 70 headphone speakers using programs developed in LabVIEW (NI) for the DAQ boards. This recording was automatically rerun every 26 min during the 12 hour bioassay period.

6. Analysis and Bioassays of Sex Pheromone Components produced by Female *T. bisselliella*

Terminal abdominal segments with pheromone glands of one-hundred 12–48 hour-old virgin females were severed and extracted for 5–15 min in hexane. GC-EAD analysis revealed 2 EAD-active components, which occurred below the detection threshold of the flame ionization detector (FIG. 10).

Figure 10:
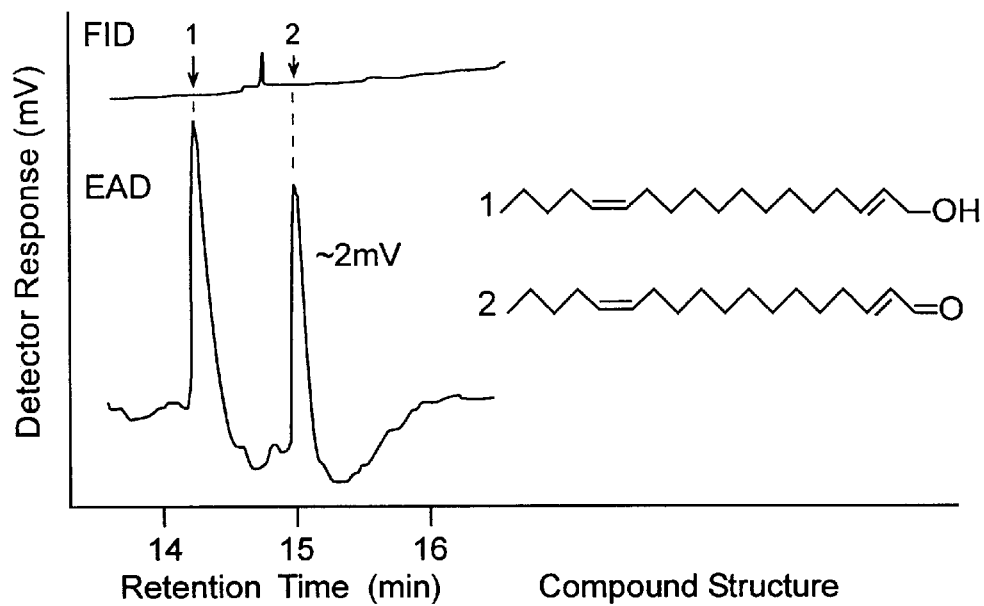
FIG. 10 illustrates flame ionization detector (FID) and electroantennographic detector (EAD: male T. bisselliella antenna) responses to one female equivalent of female T. bisselliella pheromone gland extract.

FIG. 10 illustrates flame ionization detector (FID) and electroantennographic detector (EAD: male *T. bisselliella* antenna) responses to one female equivalent of female *T. bisselliella* pheromone gland extract. EAD-active compounds 1–3 were identified as 1. (E,Z)-2,13:octadecadienol (E2,Z13–18:OH) and 2. (E,Z)-2,13:octadecadienal (E2, Z13–18:Ald). Chromatography: Hewlett Packard (HP) 5890A gas chromatograph equipped with a fused silica column (30 m×0.32 mm ID) coated with DB-23 (J & W Scientific, Folsom, Calif. 95630); linear flow velocity of carrier gas: 35 cm/sec; injector and FID detector temperature: 240° C.; temperature program: 1 min at 50° C., 10° C./min to 200° C.

Retention index calculations of EAD-active components 1 and 2 on fused silica columns coated with DB-5, DB-210, and DB-23 suggested the compounds were E2,Z13-18:OH and E2,Z13-18:Ald, respectively. GC-EAD analyses of synthetic compounds at quantities equivalent to those in pheromone gland extracts resulted in retention times of antennal responses identical for female-produced and synthetic components, confirming structural assignments.

In arena bioassay experiments 34–37 (employing the general protocol described on page 7, lines 22–31, paragraph [0041]) synthetic E2,Z13-18:OH and E2,Z13-18:Ald proved to be the sex pheromone components that attracted male *T. bisselliella*. This 2-component blend, even at very low quantity, attracted more male *T. bisselliella* than did 2 virgin females confined in a nylon mesh cage (Exp. 37) (FIG. 11).

Figure 11:
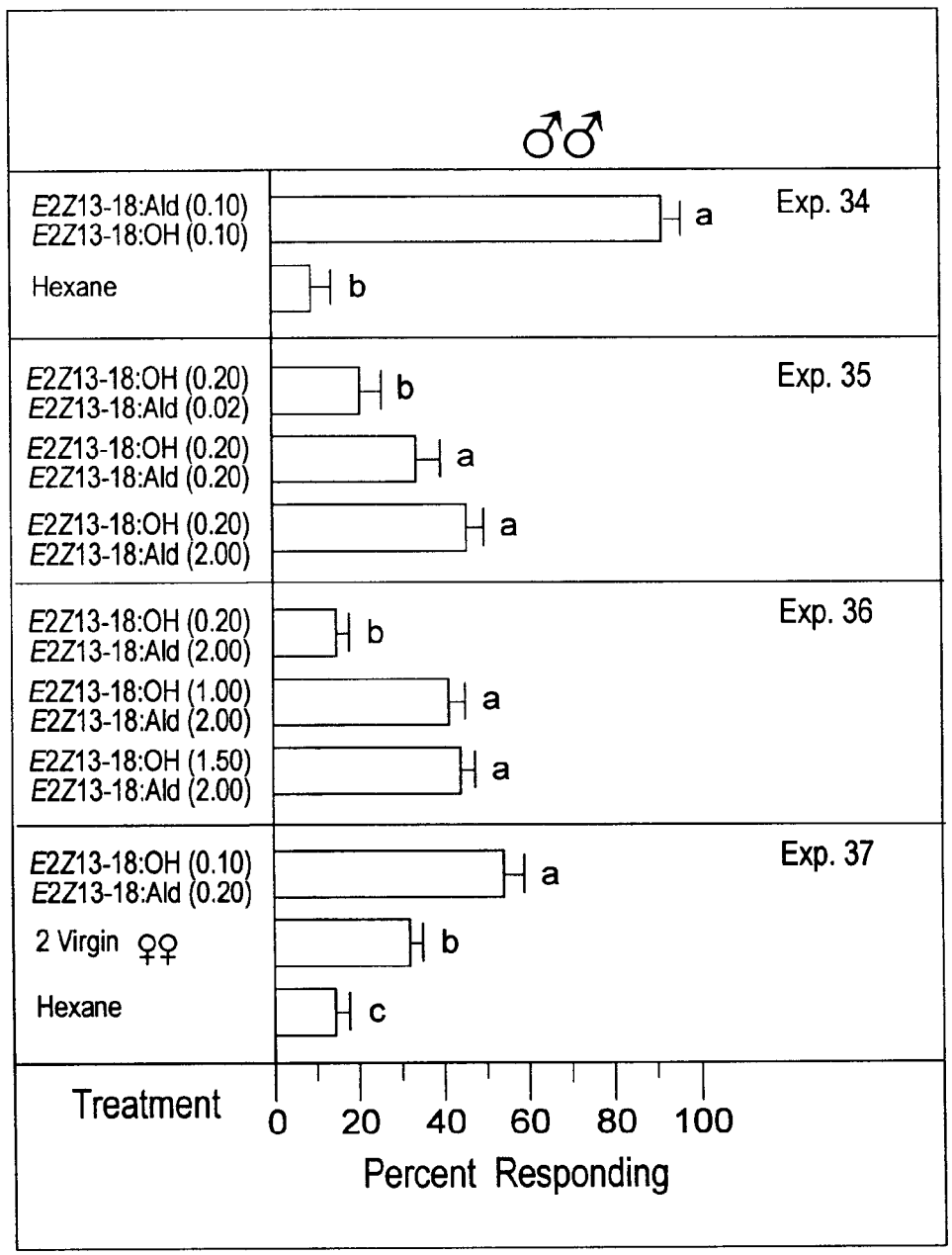
FIG. 11 illustrates graphical data of captures of male T. bisselliella in traps baited with synthetic female pheromone components.

FIG. 11 illustrates graphical data of captures of male *T. bisselliella* in traps baited with (E,Z)-2,13-octadecadienol (E2,Z13-18:OH) and (E,Z)-2,13:octadecadienal (E2,Z13-18:Ald) in various ratios, solvent, or virgin female *T. bisselliella*. Synthetic chemicals were dispensed from Whatman #1 filter paper. Females were confined in a nylon mesh cage. Bars with different letters indicate a significant difference [Wilcoxon paired-sample test (P<0.05) or Kruskal Wallis test with Tukey type non-parametric multiple comparison (P<0.05).]

7. Development of an Optimal Bait for Attraction of Male and Female *T. bisselliella*

Stimuli tested singly and in combination included: a) synthetic male pheromone components 16:Ester and Z9-16:Ester (See FIGS. 6 and 7); b) recorded sonic signals from male *T. bisselliella* (see FIGS. 8 and 9); c) synthetic female pheromone components E2,Z13-18:OH and E2,Z13-18:Ald (see FIGS. 10 and 11); d) animal pelt (=natural larval habitat, see FIG. 1); e) synthetic semiochemicals nonanal plus geranylacetone (see FIGS. 2, 3 and 4). All bioassay experiments were conducted using the general protocol described on page 7, lines 22–31, paragraph [0041].

EXAMPLE #1

Figure 12:
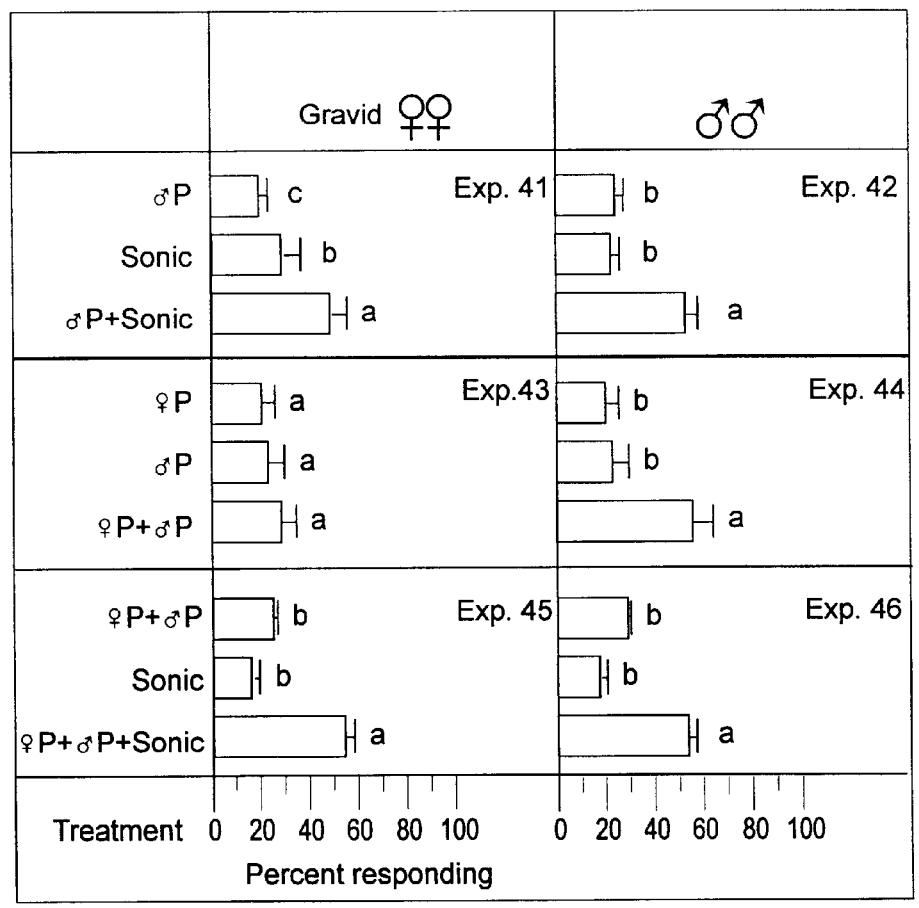
FIG. 12 illustrates graphical data of captures of male or gravid female T. bisselliella in traps baited with various test stimuli singly or in combination.

In experiments 41 and 42, synthetic male pheromone components (16:Ester and Z9-16:Ester) in combination with played-back sonic signals from male *T. bisselliella* attracted more gravid females and males than did either stimulus alone (FIG. 12).

FIG. 12 illustrates graphical data of captures of male or gravid female *T. bisselliella* in traps baited with various test stimuli singly or in combination, as follows: ♂P=synthetic male pheromone components: hexadecanoic acid methyl ester (480 ng) plus (Z)-9-hexadecenoic acid methyl ester (840 ng); ♀P=synthetic female pheromone components: (E,Z)-2,13:octadecadienol (1 ng) plus (E,Z)-2,13:octadecadienal (2 ng); Sonic=sonic signals recorded from male *T. bisselliella* (see FIG. 8). Bars with different letters indicate a significant difference [ANOVA with Tukey multiple comparison ($P<0.05$)].

In experiment 44, synthetic male pheromone in combination with synthetic female pheromone attracted more males than did male or female pheromone alone (FIG. 12). In experiments 45 and 46, female and male pheromone in combination with played back sonic signals from males attracted more gravid female and male *T. bisselliella* than did pheromonal or sonic signals alone (FIG. 12).

EXAMPLE #2

Figure 13:
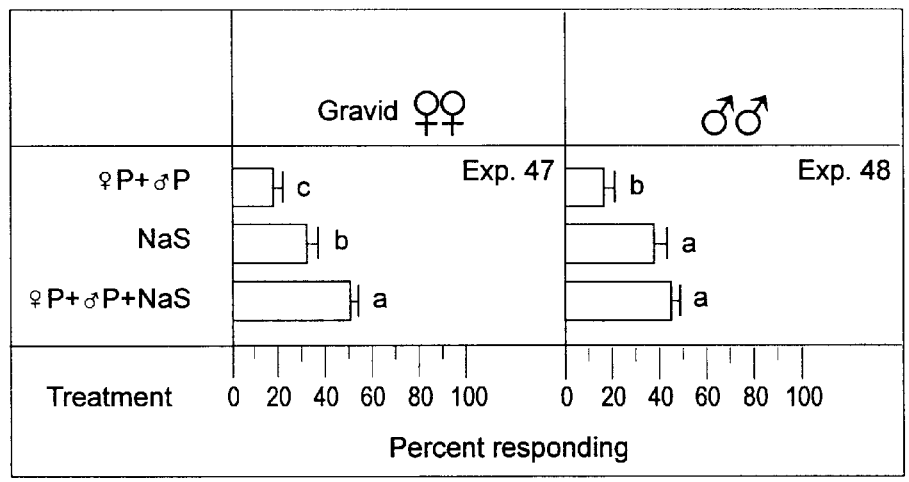
FIG. 13 illustrates graphical data of captures of male or gravid female T. bisselliella in traps baited with various test stimuli singly or in combination.

In experiments 47 and 48, animal pelt (NaS) attracted more gravid female and male *T. bisselliella* than did synthetic female plus male pheromone (♂P+♀P); the combination of animal pelt plus male and female pheromone was most attractive (FIG. 13).

FIG. 13 illustrates graphical data of captures of male or gravid female *T. bisselliella* in traps baited with various test stimuli singly or in combination as follows: ♀P=synthetic female pheromone components: (E,Z)-2,13:octadecadienol (1 ng) plus (E,Z)-2,13:octadecadienal (2 ng); ♂P=synthetic male pheromone components: hexadecanoic acid methyl ester (480 ng) plus (Z)-9-hexadecenoic acid methyl ester (840 ng); NaS=natural semiochemicals: dried muskrat pelt (50 cm$^2$). Bars with different letters indicate a significant difference [ANOVA with Tukey multiple comparison of arcsine transformed proportions ($\alpha=0.05$)].

EXAMPLE #3

Figure 14:
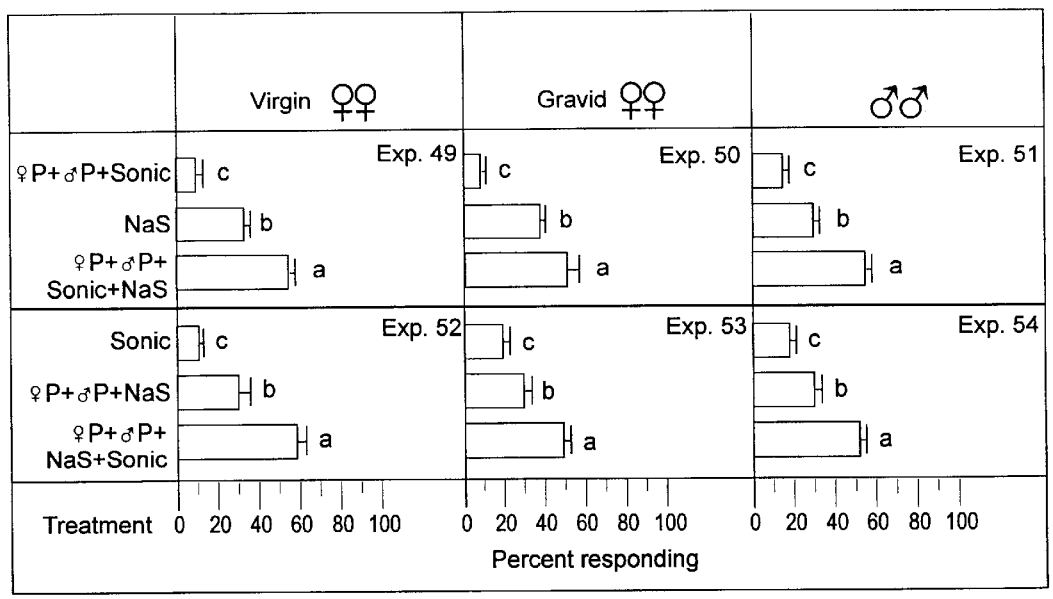
FIG. 14 illustrates graphical data of captures of virgin female, gravid female or male T. bisselliella in traps baited with various test stimuli singly or in combination.

In experiments 49, 50 and 51, animal pelt (NaS) attracted more virgin female, gravid female, and male *T. bisselliella* than did a combination of female pheromone (♀P), male pheromone (♂P) and played-back sonic signals from male *T. bisselliella*; all stimuli combined (♀P+♂P+Sonic+NaS) were significantly most attractive (FIG. 14).

FIG. 14 illustrates graphical data of captures of virgin female, gravid female or male *T. bisselliella* in traps baited with various test stimuli singly or in combination as follows: ♀P=synthetic female pheromone components: (E,Z)-2,13-octadecadienol (1 ng) plus (E,Z)-2,13:octadecadienal (2 ng); ♂P=synthetic male pheromone components: hexadecanoic acid methyl ester (480 ng) plus (Z)-9-hexadecenoic acid methyl ester (840 ng); NaS=natural semiochemicals: dried muskrat pelt (50 cm$^2$). Bars with different letters indicate a significant difference [ANOVA with Tukey multiple comparison of arcsine transformed proportions ($\alpha=0.05$)].

Similarly, in experiments 52, 53, and 54 all stimuli combined (♀P+♂P+Sonic+NaS) attracted more virgin female, gravid female, and male *T. bisselliella* than did a combination of chemical stimuli (♀P+♂P+NaS) or played back sonic signals (Sonic) from male *T. bisselliella* (FIG. 14).

EXAMPLE #4

Figure 15:
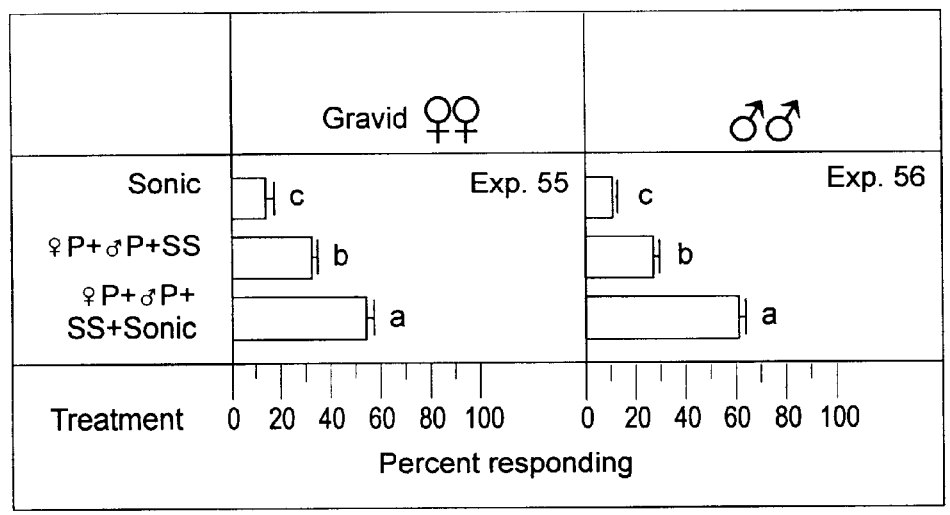
FIG. 15 illustrates graphical data of captures of gravid female or male T. bisselliella in traps baited with various test stimuli singly or in combination.

In experiments 55 and 56, a combination of synthetic female pheromone (♀P), synthetic male pheromone (♂P), synthetic semiochemicals (SS: identified from animal pelt; see FIG. 4), and played-back sonic signals (Sonic) from male *T. bisselliella* attracted more gravid female and male *T. bisselliella* than did chemical (♀P+♂P+SS) or sonic signals alone (FIG. 15).

FIG. 15 illustrates graphical data of captures of female and male *T. bisselliella* in traps baited with stimuli singly or in combination as follows: ♀P=synthetic female pheromone components: (E,Z)-2,13:octadecadienol (1 ng) plus (E,Z)-2,13:octadecadienal (2 ng); ♂P=synthetic male pheromone components: hexadecanoic acid methyl ester (480 ng) plus (Z)-9-hexadecenoic acid methyl ester (840 ng); SS=synthetic semiochemicals: geranylacetone (44 ng) and nonanal (3.5 μg) (see FIG. 4). Bars with different letters indicate a significant difference [ANOVA with Tukey multiple comparison of arcsine transformed proportions ($\alpha=0.05$)].

EXAMPLE #5

Figure 16:
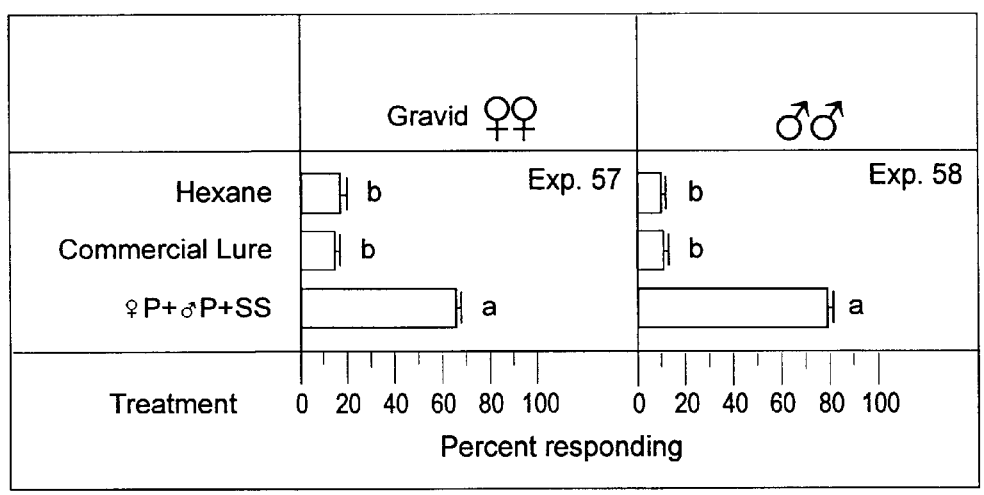
FIG. 16 illustrates graphical data of captures of gravid female or male T. bisselliella in traps baited with newly identified synthetic attractants, a commercial bait or a solvent control.
Figure 17:
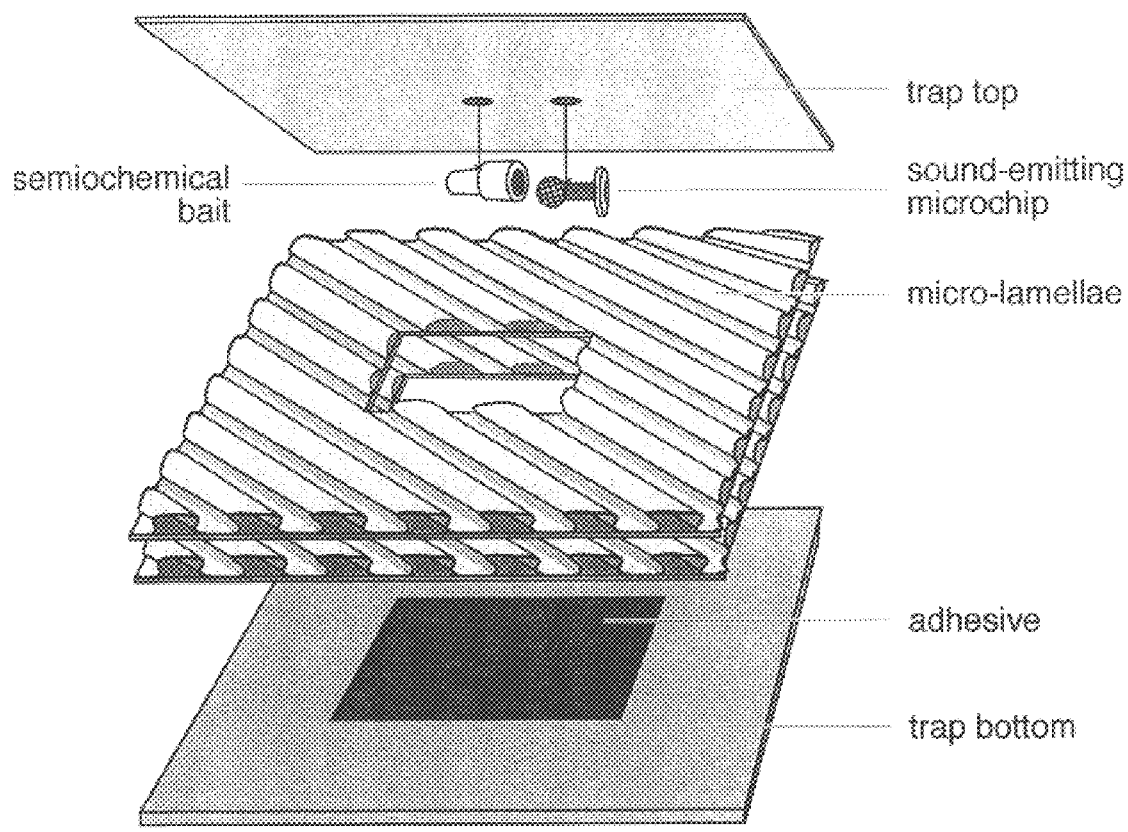
FIG. 17 illustrates a potential trap design, said trap baited with a sound-emitting micro-chip and a semiochemical dispenser for attraction and capture of T. bisselliella and other keratin-feeding insects.

In experiment 57, a combination of synthetic male pheromone (♂P), synthetic female pheromone (♀P), and synthetic semiochemicals (SS) identified from larval habitat attracted more female and male *T. bisselliella* than did a commercial lure, which in turn was not more attractive than a solvent (hexane) control stimulus (FIG. 16).

FIG. 16 illustrates graphical data of captures of female and male *T. bisselliella* in traps baited with the following stimuli: ♀P=synthetic female pheromone components: (E,Z)-2,13:octadecadienol (1 ng) plus (E,Z)-2,13:octadecadienal (2 ng); ♂P=synthetic male pheromone components: hexadecanoic acid methyl ester (480 ng) plus (Z)-9-hexadecenoic acid methyl ester (840 ng); SS=synthetic semiochemicals: synthetic geranylacetone (44 ng) and nonanal (3.5 μg) (see FIG. 4). The commercial lure consisted of (E,Z)-2,13:octadecadienal (2 ng) plus (E)-2-octadecanal (1 ng). Hexane served as the solvent control. All chemicals were dispensed from Whatman #1 filter paper. Bars with different letters indicate a significant difference [ANOVA with Tukey multiple comparison of arcsine transformed proportions ($\alpha=0.05$)].

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

References

1. HILL, D. S. 1990. Pests of stored products and their control. Belhaven Press, London.
2. MALLIS, A. 1969. Handbook of pest control: the behavior, life history, and control of household pests. *Mac Nair-Dorland Company*: New York.
3. STORY, K. O. 1985. Approaches to pest management in museums. Smithsonian Institution. pp 33–38.
4. METCALF, R. L. and R. A. METCALF. 1994. Attractants, repellents, and genetic control in pest management. In: R. L. Metcalf and W. H. Luckman (eds.) *Introduction to Insect Pest Management* Third Edition. John Wiley and Sons Inc: New York. pp. 355–356.
5. HINTON, H. E. 1956. The larvae of species of Tineidae of economic importance. *Bull. Entomol. Res.* 47:251–346.
6. BRY, R. E., J. H. LANG and R. E. BOATRIGHT. 1981. Feeding by larvae of three species of fabric insects on wool/synthetic blend fabrics. *J. Georgia Entomol. Soc.* 17:280–282.
7. WOODROFFE, G. E. 1953. An ecological study of the insects and mites in the nests of certain birds in Britain. *Bull. Entomol. Res.* 44:739–772.
8. BORNEMISSZA, G. F. 1957. An analysis of arthropod succession in carrion and the effect of its decomposition on the soil fauna. *Aust. J. Zool.* 5:1–12.
9. BROKERHOF, A. W., R. MORTON, H. J. BANKS. Time-mortality relationships for different species and developmental stages of clothes moths (Lepidoptera: Tineidae) exposed to cold. *J. Stor. Prod. Res.* 29:277–282.
10. GERARD, P. J. and L. D. RUF. 1995. Effect of a Neem (Azadirachta indica A. Juss, Meliaceae) extract on survival and feeding of larvae of four keratinophagous insects. *J. Stor. Prod. Res.* 31: 111–116.
11. GERARD, P. J., N. B. PERRY, L. D. RUF, L. M. FOSTER. 1993. Antifeedant and insecticidal activity of compounds from *Pseudowintera colorata* (Winteraceae) on the Webbing clothes moth, *Tineola bisselliella* (Lepidoptera: Tineidae) and the Australian carpet beetle, *Anthrenocerus australis* (Coleoptera: Dermestidae). *Bull. Entomol. Res.* 83:547–552.
12. WILSON, H. F. 1940. Lures and traps to control clothes moths and carpet beetles. *J. Econ. Ent.* 33:651–653.
13. KAN E. and Y. WAKU. 1985. Analysis of oviposition preference in the webbing clothes moth, *Tineola bisselliella* HUM. (Lepidoptera: Tineidae) *Appl. Ent. Zool.* 20:322–330.
14. TRANYIER, R. M. M., R. K. SCHUMACHER, and D. M. LAU, 1994. Oviposition site selection by *Tineola bisselliella*, Tinea spp. (Lepidoptera: Tineidae) and *Anthrenus flavipes* (Coleoptera: Dermestidae). *J. Stor. Prod. Res.* 30:321–329.
15. YAMAOKA, R., Y. SHIRAISHI, T. UENO, Y. KUWAHARA, H. FUKAMI. 1985. Structural elucidation of Koiganal I and II, the sex pheromone of the webbing clothes moth, using capillary GC/MS. Mass Spec. 33:189–195.
16. Cox, P. D., D. B. PINNIGER, D. MUELLER. Monitoring populations of the webbing clothes moth, *Tineola bisselliella*, using pheromone lures. In: Wildey, K. B. (Ed.) Proceedings of the second International Conference on Insect Pests in the Urban Environment. Pp. 541–545.
17. TREMATERRA, P. and F. FONTANA. 1996. Monitoring of Webbing Clothes Moth *Tineola bisselliella* (Hummel), by sex pheromone. *Anz. Schädlingskunde Pflanzenschutz Umweltschutz.* 69:119–121.
18. HALL, L. B. 1984. Ultrasonic pest control device. U.S. Pat. No. 4,484,315.
19. HALL, L. B. 1986. Pest control apparatus. U.S. Pat. No. 4,616,351.
20. NEUKOM, A. J., D. REINEHR, W. SCHMID. 1991. Moth- and beetle-proofing agents. U.S. Pat. No. 5,057,539.
21. BEHRENZ, W. and G. SAVETTI. 1989. Agents for combating *Tineola bisselliella*. U.S. Pat. No. 4,845,131.
22. BOGER, M., B. de SOUS, D. REINEHR, W. SCHMID, H. REMPFLER, H. TOBLER. 1988. Process for protecting keratinous material from attack by insects feed on keratin with pyridyloxytrifluoromethanesulfonanilides. U.S. Pat. No. 4,731,090.
23. de SOUSA, B., U. BURCKARDT, J. J. GALLAY, M. KUHNE, E. BERIGER, D. REINEHR. 1986. Mothproofing and beetleproofing composition: 5-(pyridyloxy- or thiothenylcarbamoyl)barbituric acid. U.S. Pat. No. 4,602,912.
24. de SOUSA, R. MUNTWYLER, W. SCHMID. 1981. Method of protecting keratinous material from attack by insects that feed on keratin by treatment with 5-phenylcarbamoylbarbituric acid compounds. U.S. Pat. No. 4,283,444.
25. CARLSON, G. R. 1994. Wool protecting compositions and methods. U.S. Pat. No. 5,358,967.
26. BOGER, M., D. REINEHR, B. de SOUSA, W. SCHMID. 1987. Process for protecting keratinous material from attack by insects that feed on keratin and novel phenoxytrifluoromethanesulfoanilides. U.S. Pat. No. 4,646,673.
27. BLAZER, J. S. 1996. Moths inhibiting multigarment clothes hanger. U.S. Pat. No. 5,582,334.
28. ARN, H., E. STÄDLER, and S. RAUSCHER. 1975. The electroantennographic detector—a selective and sensitive tool in the gas chromatographic analysis of insect pheromones. *Z. Naturforsch.* 30c:722–725.
29. VET, L. E. M. 1983. Host-habitat location through olfactory cues by *Leptopilina clavipes* (Hartig) (Hym.: Eucoilidae), a parasitoid of fungivorous Drosophila: the influence of conditioning. *Netherlands Journal of Zoology.* 33:225–248.

What is claimed is:

1. A composition of chemicals for manipulating the behaviour of clothes moths, said composition comprising two or more chemicals in all possible combinations and ratios selected from the group consisting of:

1) (E,Z)-2,13-octadecadienal;

2) (E,Z)-2,13:octadecadienol;

3) hexadecanoic acid methyl ester;

4) (Z)-9-hexadecenoic acid methyl ester;

5) nonanal;

6) geranylacetone;

7) octanal;

8) decanal;

9) nonenal;

10) octenal;

11) decenal.

2. A composition as claimed in claim 1 wherein the composition is contained in, or released from, slow release devices.

3. A composition as claimed in claim 1 wherein the composition is contained in, and released from, a trap that captures attracted *T. bisselliella*.

4. A fur or fabric feeding insect bait and trap for deployment in an area containing fur or fabric, said bait incorporating a composition of chemicals as claimed in claim 1, and said trap having at least one opening which enables the insects to enter the trap and a harder or retainer which prevents the insects from leaving the trap.

5. A method of manipulating the behaviour of insects that feed on fur or fabric which comprises exposing the insects to one or more chemicals as claimed in claim 1.

6. A method of diagnosing whether protection of fur or fabric is warranted, comprising exposing the fir or fabric to a composition as claimed in claim 1 and determining whether any fur or fabric consuming insects are attracted by the composition.

7. A method of protecting fur or fabric from attack by fur or fabric consuming insects by deploying proximate to the fur or fabric a composition as claimed in claim 1.

8. A combination of chemical and sonic signals for manipulating the behaviour of clothes moths, said combination comprising a composition of two or more chemicals in all combinations and ratios selected from the group consisting of:
   1) (E,Z)-2,13:octadecadienal;
   2) (E,Z)-2,13:octadecadienol;
   3) hexadecanoic acid methyl ester;
   4) (Z)-9-hexadecenoic acid methyl ester;
   5) nonanal;
   6) geranylacetone;
   7) octanal;
   8) decanal;
   9) nonenal;
   10) octenal;
   11) decenal, and a sonic signal of one or more frequencies in all combinations and ratios selected from the group consisting of:
      1) 50+/−10 Hz;
      2) 110+/−20 Hz;
      3) 70+/−10 Hz;
      4) 140+/−10 Hz;
      5) 165+/−30;
      6) 220+/−40;
      7); 280+/"40 Hz.

9. A combination as claimed in claim 8 wherein the chemical composition is contained in, and released from, a trap that captures attracted *T. bisselliella*, and the sonic signal is generated by a sonic apparatus that is contained in or associated with the trap that captures attracted *T. bisselliella*.

10. A combination as claimed in claim 9 wherein the sonic apparatus is an electronically activated sonic microchip.

11. A fir or fabric feeding insect bait and trap for deployment in an area containing fur or fabric, said bait incorporating a combination as claimed in claim 8, and said trap having at least one opening which enables the insects to inater the trap and a barrier or retainer which prevents the insects from leaving the trap.

12. A method of manipulating the behaviour of insects that feed on fur or fabric which comprises exposing the insects to one or more chemicals or sonic signals as claimed in claim 8.

13. A method of diagnosing whether protection of fur or fabric is warranted, comprising exposing the fur or fabric to a combination as claimed in claim 8 and determining whether any fur or fabric consuming insects are attracted by the combination.

14. A method of protecting fur or fabric from attack by fur or fabric consuming insects by deploying proximate to the fur or fabric a combination as claimed in claim 8.

15. An apparatus for attracting clothes moths, said apparatus containing a composition comprising two or more chemicals in all possible combinations and ratios selected from the group consisting of:
   1) (E,Z)-2,13:octadecadienal;
   2) (E,Z)-2,13;octadecadienol;
   3) hexadecanoic acid methyl ester;
   4) (Z)-9-hexadecenoic acid methyl ester;
   5) nonanal;
   6) geranylacetone;
   7) octanal;
   8) decanal;
   9) nonenal;
   10) octenal;
   11) decenal.

16. An apparatus as claimed in claim 15 wherein the apparatus contains an insect capturing adhesive.

17. An apparatus for attracting clothes moths, said apparatus containing a combination of chemical and sonic signals for manipulating the behaviour of clothes moths, said combination comprising a composition of two or more chemicals in all combinations and ratios selected from the group consisting of:
   1) (E,Z)-2,13:octadecadienal;
   2) (E,Z)-2,13:octadecadienol;
   3) hexadecanoic acid methyl ester;
   4) (Z)-9-hexadecenoic acid methyl ester;
   5) nonanal;
   6) geranylacetone;
   7) octanal;
   8) decanal;
   9) nonenal;
   10) octenal;
   11) decenal, and a sonic signal of one or more frequencies in all combinations and ratios selected from the group consisting of:
      1) 50+/−10 Hz;
      2) 110+/−20 Hz;
      3) 70+/−10 Hz;
      4) 140+/−10 Hz;
      5) 165+/−30;
      6) 220+/−40;
      7) 280+/−40 Hz.

18. An apparatus as claimed in claim 17 wherein the apparatus contains an insect capturing adhesive.

* * * * *